(12) United States Patent
Zhang et al.

(10) Patent No.: US 9,017,621 B1
(45) Date of Patent: *Apr. 28, 2015

(54) PREPARATION SYSTEM AND METHOD

(71) Applicant: The United States of America as represented by the Administrator of the National Aeronautics and Space Administration, Washington, DC (US)

(72) Inventors: Ye Zhang, League City, TX (US); Honglu Wu, Friendswood, TX (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 7 days.

This patent is subject to a terminal disclaimer.

(21) Appl. No.: 13/791,290

(22) Filed: Mar. 8, 2013

Related U.S. Application Data

(60) Provisional application No. 61/680,075, filed on Aug. 6, 2012.

(51) Int. Cl.
| | | |
|---|---|---|
| *G01N 21/75* | (2006.01) | |
| *C07H 21/00* | (2006.01) | |
| *C12M 1/00* | (2006.01) | |

(52) U.S. Cl.
CPC ............... *C12M 45/09* (2013.01); *C07H 21/00* (2013.01); *G01N 21/75* (2013.01)

(58) Field of Classification Search
CPC .............................. C07H 21/00; G01N 21/75
USPC ......................................... 536/25.4; 422/417
See application file for complete search history.

(56) References Cited

U.S. PATENT DOCUMENTS

| | | | |
|---|---|---|---|
| 4,202,309 A * | 5/1980 | Burke ......................... | 123/179.8 |
| 6,110,730 A | 8/2000 | Sams et al. | |
| 7,781,159 B2 | 8/2010 | Gazenko | |
| 2005/0260569 A1 | 11/2005 | Houde et al. | |
| 2009/0280470 A1 | 11/2009 | Fare et al. | |
| 2010/0248350 A1 | 9/2010 | Gazenko | |

* cited by examiner

*Primary Examiner* — Ardin Marschel
(74) *Attorney, Agent, or Firm* — Kurt G. Hammerle

(57) ABSTRACT

Systems and methods for preparing a sample for further analysis are provided. The system can include an enclosure. A membrane can be disposed within the enclosure. First and second reservoirs can be disposed within the enclosure, and at least one of the first and second reservoirs can be adapted to have a reagent disposed therein. A valve can be disposed within the enclosure and in fluid communication with the first or second reservoirs or both. The valve can also be in fluid communication with the membrane. The valve can be adapted to selectively regulate the flow of the reagent from the first reservoir, through the membrane, and into the second reservoir.

17 Claims, 10 Drawing Sheets

US 9,017,621 B1

PREPARATION SYSTEM AND METHOD

CROSS-REFERENCE TO RELATED APPLICATIONS

This application claims the benefit of a related U.S. Provisional Application Ser. No. 61/680,075 filed Aug. 6, 2012, entitled "Pre-Polymerase Chain Reaction Preparation Kit," the disclosure of which is incorporated by reference herein in its entirety.

ORIGIN OF THE INVENTION

The invention described herein was made in the performance of work under a NASA contract and is subject to the provisions of Section 305 of the National Aeronautics and Space Act of 1958, Public Law 85-568 (6052 Stat. 435; 42 U.S.C. 233605).

BACKGROUND

Field

Embodiments described herein generally relate to apparatus, systems, and methods for the isolation and/or preparation of biological and non-biological samples for further analysis, such as pre-analysis sample-reagent mixing, distributing, and loading.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

Systems and methods for releasing biological and non-biological samples of interest, such as nucleic acids or other samples, from a membrane are disclosed. The system, which may be self-enclosed and automated for use in space or terrestrial environments, can include an enclosure. A membrane can be disposed within the enclosure. First and second reservoirs can be disposed within the enclosure, and at least one of the first and second reservoirs can have a reagent disposed therein. A valve, such as a multi-way valve, can be disposed within the enclosure and in fluid communication with the first or second reservoirs, or both. The valve can also be in fluid communication with the membrane. The valve can be adapted to selectively regulate the flow of the reagent from the first reservoir, through the membrane, and into the second reservoir. The system can be used for sample-reagent mixing, distributing, and loading. In one embodiment, when the system is used, an analyte or other sample can be isolated or prepared for further analysis, such as real-time polymerase chain reaction, without exposure to its external environment.

The method can include flowing a first reagent with liquid samples through a first flow path between a first reservoir and a second reservoir. The first flow path can extend through a valve, or a valve and a membrane. An analyte of interest, such as nucleic acids or other samples, can be released from the membrane when contacted with the first reagent to form a first mixture including the first reagent and the released nucleic acids or other samples. Or, liquid samples can be directly introduced to the second reservoir from the first reservoir through the valve. The valve can be rotated to form a second flow path between the second reservoir and a third reservoir through the valve. At least a portion of the first mixture can flow through the second flow path and into the third reservoir containing a second reagent to form a second mixture. The method can be performed to enable elution, dilution, mixing, distribution, or loading of a sample.

DETAILED DESCRIPTION

Figure 1:
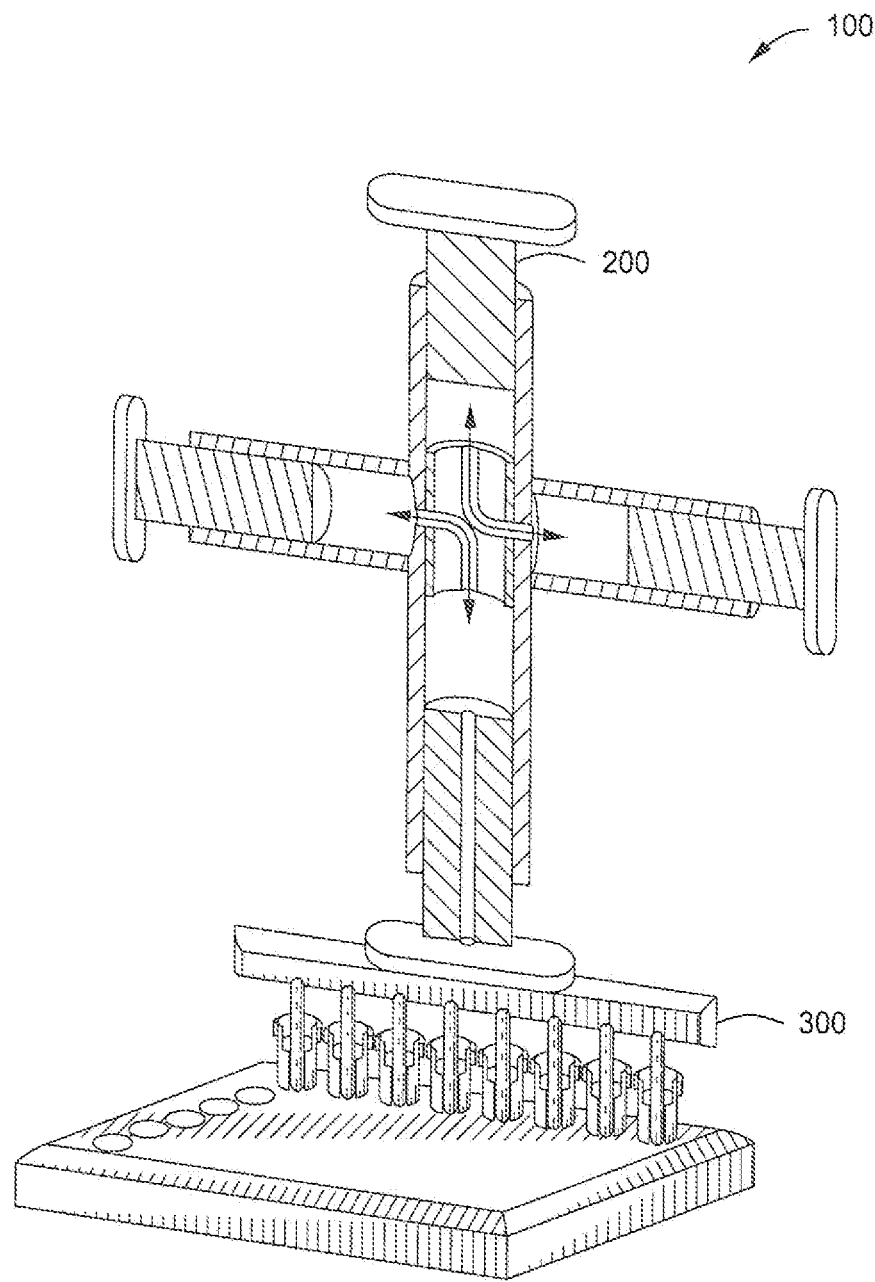
FIG. 1 depicts a cross-sectional perspective view of an illustrative sample preparation system, according to one or more embodiments described.

FIG. 1 depicts a cross-sectional perspective view of an illustrative sample preparation system 100, according to one or more embodiments described herein. The sample preparation system 100 can include one or more elution/sample preparation assemblies 200 and one or more distribution assemblies 300. The sample preparation system 100 is a pipette-free, closed system adapted to limit or prevent exposure to an external environment. In one embodiment, the sample preparation system 100 can be used in a microgravity environment. As a closed system, fluid disposed within the system 100 does not escape or leak out, as would occur with traditional open-ended pipettes, particularly when used in microgravity environments in space.

Figure 2A:
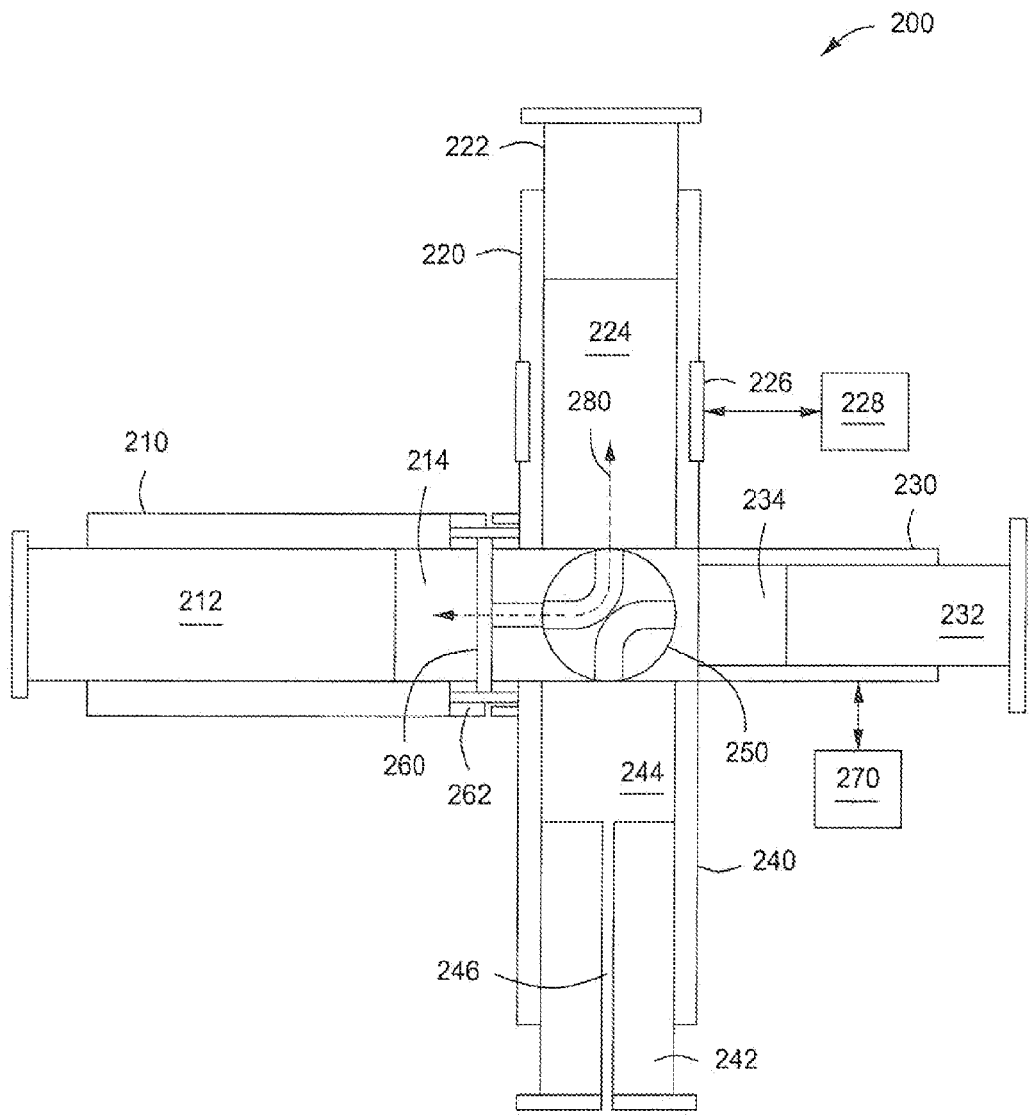
FIGS. 2A-2C depict cross-sectional views of the preparation assembly depicted in FIG. 1 during a process for preparation of a sample, according to one or more embodiments described.
Figure 2B:
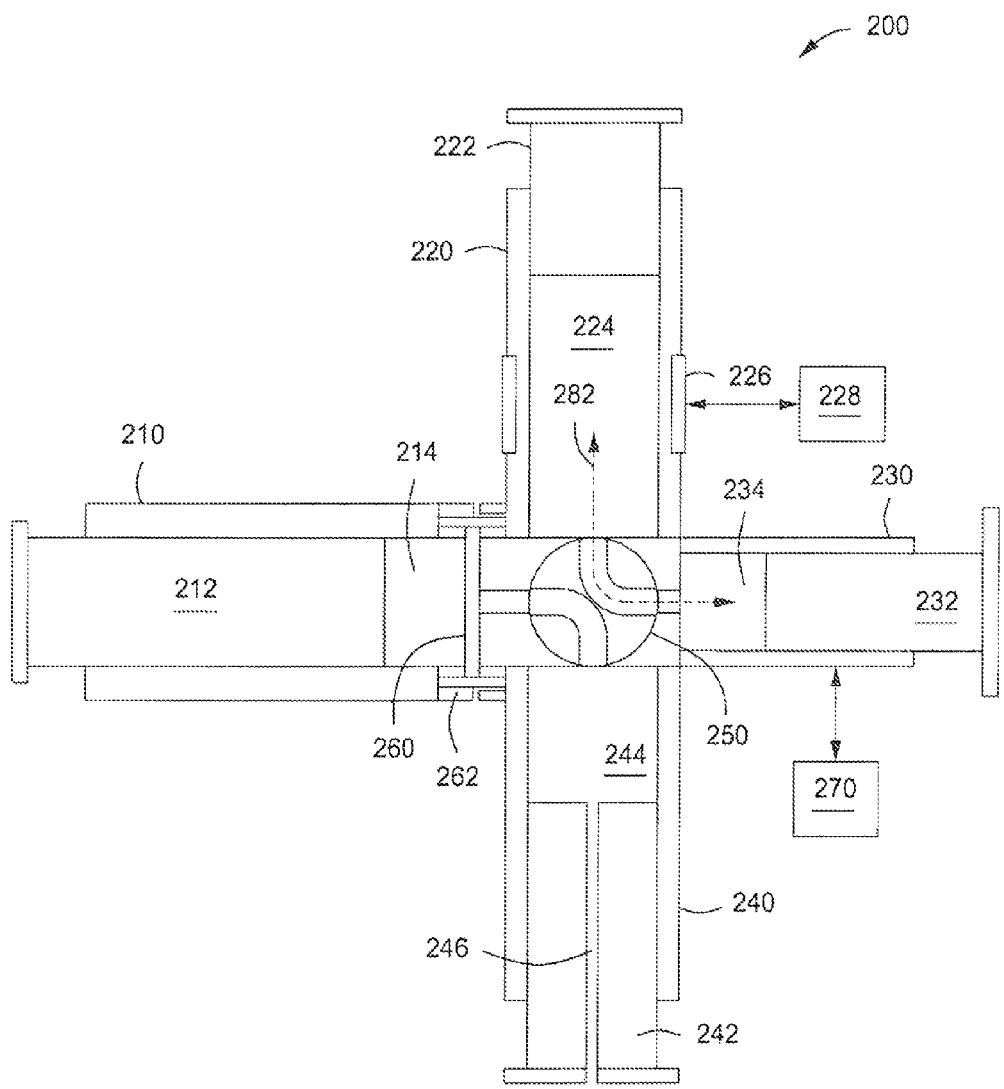
Figure 2C:
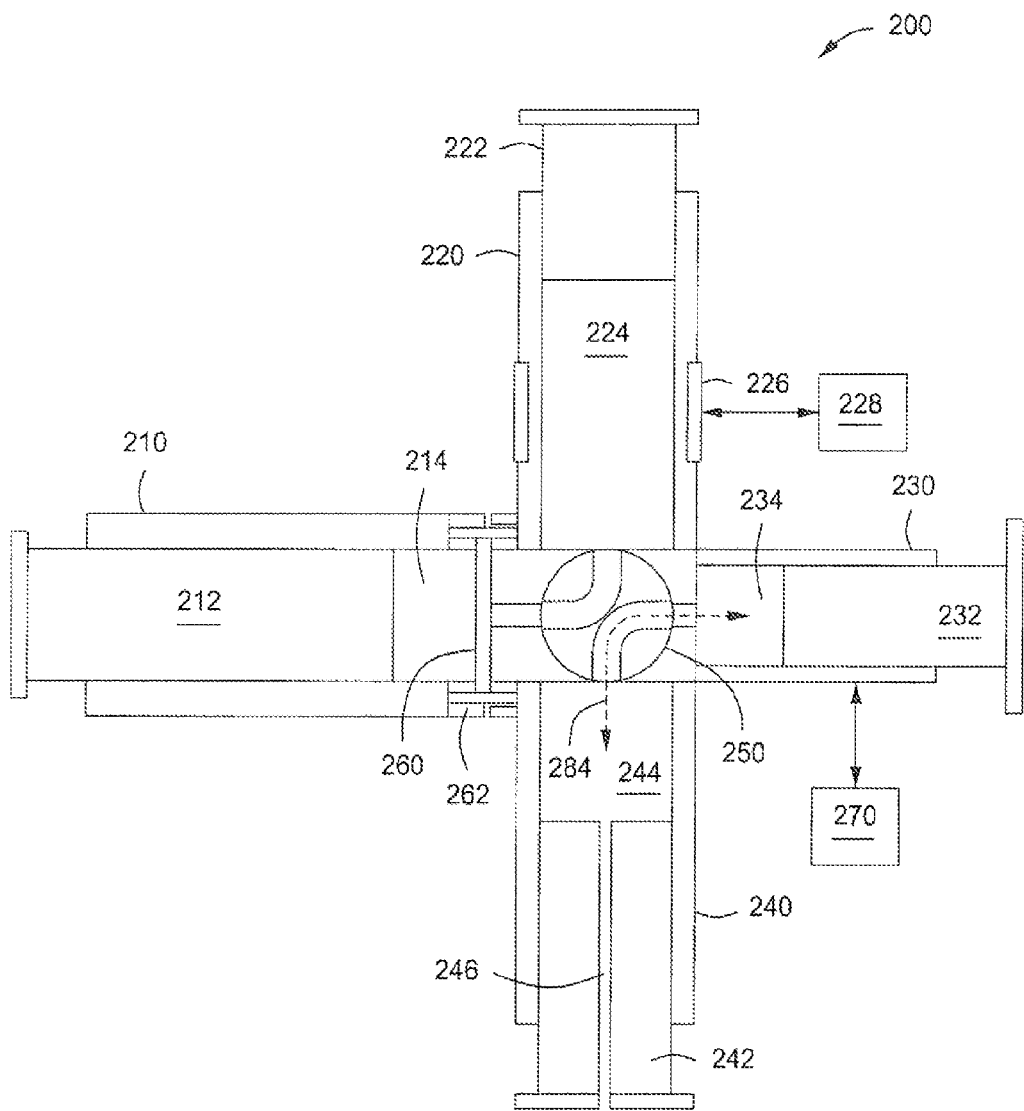

FIGS. 2A-2C depict cross-sectional views of the preparation assembly 200 depicted in FIG. 1 during a process for preparation of a sample, according to one or more embodiments. The preparation assembly 200 can include one or more injectors (four are shown 210, 220, 230, 240), one or more valves (one is shown 250), and one or more membranes (one is shown 260). Although not shown, in at least one embodiment, the preparation assembly 200 can include two injectors 210, 220 having the membrane 260 disposed therebetween. In this embodiment, the additional injectors 230, 240 and the valve 250 can be omitted.

The injectors 210, 220, 230, 240 can include one or more components. For example, each injector 210, 220, 230, 240 can have a chamber or reservoir 214, 224, 234, 244 disposed therein, respectively. Each injector 210, 220, 230, 240 can also have a piston 212, 222, 232, 242, respectively, adapted to slide axially therein. Axial movement of the piston 212, 222, 232, 242 within its respective injector 210, 220, 230, 240 can push fluid out of its respective reservoir 214, 224, 234, 244 and into one of the reservoirs 214, 224, 234, 244 of another injector. Similarly, axial movement of the piston 212, 222, 232, 242 within its respective injector 210, 220, 230, 240 can also draw fluid into its respective reservoir 214, 224, 234, 244 from one of the reservoirs 214, 224, 234, 244 of another injector.

At least one of the pistons 212, 222, 232, 242 can have a bore formed axially therethrough such that the bore forms a path of fluid communication between the reservoir and the exterior of the injector 210, 220, 230, 240. As shown in FIG. 2A, the fourth piston 242 has a bore 246 formed therethrough. The bore 246 can allow fluid to be injected into or withdrawn from the reservoir 244 of the fourth injector 240, as described in more detail below.

At least one of the injectors 210, 220, 230, 240 can have an interface 226 adapted to receive a light source 228, such as a spectrophotometer, illuminometer, and/or fluorometer. The light source 228 can be adapted to measure the reflection, emission, or transmission properties of the fluid within the reservoir 224 as a function of its wavelength. The interface 226 can be any shape, including round, flat, or the like that fits the adapted light source 228. In at least one embodiment, the light source 228 can be a nanodrop (ND) 2000c spectrophotometer.

The valve 250 can be disposed within the preparation assembly 200 and coupled to at least one of the injectors 210, 220, 230, 240 such that the reservoirs 214, 224, 234, 244 of the injectors 210, 220, 230, 240 can be in fluid communication with one another through the valve 250. In at least one embodiment, one or more of the injectors 210, 220, 230, 240 can be operatively connected, such as by threadable engagement or other method of attachment, with the valve 250. Although not shown, tubing having a diameter similar to the diameter of the flow path through the valve 250, e.g., 15-gauge, can be coupled to and disposed between the injectors 210, 220, 230, 240 and the valve 250 to provide more flexibility in the layout or configuration of the preparation assembly 200.

The valve 250 can include a rotatable housing having at least one bore formed therethrough. In FIGS. 1 and 2A-2C, the valve 250 has two bores shown, but one bore will be discussed in further detail with reference to the FIGS. 2A-2C during operation of the preparation system. The valve 250 can be actuated or rotated to provide more than one path of fluid communication among the plurality of reservoirs 214, 224, 234, 244, i.e., the valve may be considered to be a "multi-way" valve. In one embodiment, a suitable valve 250 can be or include those manufactured by the Hamilton Company in Reno, Nev.

In at least one embodiment, the membrane 260 can have isolated nucleic acids, such as DNA and/or RNA disposed thereon. The term "membrane," as used herein, refers to any material or layer(s) of material that acts as a selective barrier, allowing fluids and some particles to pass therethrough, while other particles are not allowed to pass therethrough, and are instead retained therein.

The membrane 260 can be disposed within a membrane support assembly 262, and the membrane support assembly 262 can be disposed within the preparation assembly 200. In at least one embodiment, the membrane support assembly 262 can be disposed between one of the injectors 210, 220, 230, 240 and the valve 250. For example, the membrane support assembly 262 can be operatively connected, such as by being threadably engaged or otherwise attached, with the first injector 210 and the valve 250. The support assembly 262 can be perforated and disposed adjacent to opposing surfaces of the membrane 260. As such, fluid can pass or flow through the membrane 260 and the membrane support assembly 262.

A suitable membrane 260 can include one or more micropores. In one embodiment, the micropores can have an average pore diameter ranging from a low of about 0.2 μm, about 0.4 μm, or about 0.6 μm to a high of about 1 μm, about 2 μm, about 3 μm, about 4 μm, about 5 μm, or more for RNA/DNA isolation and/or preparation. However, for other applications, the micropores can have an average pore diameter ranging from a low of about 0.0001 μm, about 0.001 μm, or about 0.01 μm to a high of about 0.05 μm, about 0.1 μm, or about 0.2 μm (e.g., for protein isolation or separation), or from a low of about 10 μm, about 20 μm, or about 30 μm to a high of about 50 μm, about 75 μm, or about 100 μm (e.g., for filtering single cell suspensions). The membranes can also be used for binding, isolating, and separating specific molecules and particles, isolating specific types of cells, and reagent sterilization.

The membrane 260 can be, but is not limited to, a proteinase membrane, a homogenizing membrane, a filtering membrane, a binding membrane, or any combination thereof. For example, the membrane 260 can be a binding membrane having precipitated nucleic acids bound thereto. Suitable membranes 260 can also include a solid surface functionalized with immobilized active enzymes and high density enzyme surfaces. More specifically, suitable membranes 260 can include a solid surface functionalized with immobilized proteinase, such as trypsin, chymotrypsin, endoproteinase GluC, papain, endoproteinase pepsin, proteinase K, and the like. Suitable solid surfaces can also include glass fiber, glass fiber treated with oleophobic coatings, silica particles or beads, silica particles or beads coated with oleophobic coatings, nylon, and other oleophobic materials, and the like. For example, suitable membranes can include the DigesTip produced by ProteoGen Bio in Siena, Italy. Suitable membranes 260 can also include, but are not limited to, membranes found in a standard kit for the purification of DNA or RNA, such as the commercially available kit sold by the manufacturer Qiagen, (e.g., DNeasy Blood and Tissue Kit, RNeasy Mini Kit, RNeasy Protect Mini Kit, and RNeasy Plant Mini Kit). In at least one embodiment, the surface can be coated with complementary oligo nucleotides, antibodies, covalently or non-covalently binding to target molecules, and/or any particles and membranes used for separating molecules based on size and isoelectric point.

One or more control systems 270 can be in communication with the preparation assembly 200. In at least one embodiment, the control system 270 can be adapted to measure the volume of fluid within the reservoirs 214, 224, 234, 244, measure the concentration of nucleic acids disposed in the fluid within the reservoirs 214, 224, 234, 244, and/or actuate the pistons 212, 222, 232, 242 to cause a calculated amount of fluid to flow between reservoirs 214, 224, 234, 244. The control system 270 can serve as a digital volume control and automatic distributor of fluid within the preparation assembly 200.

Figure 3:
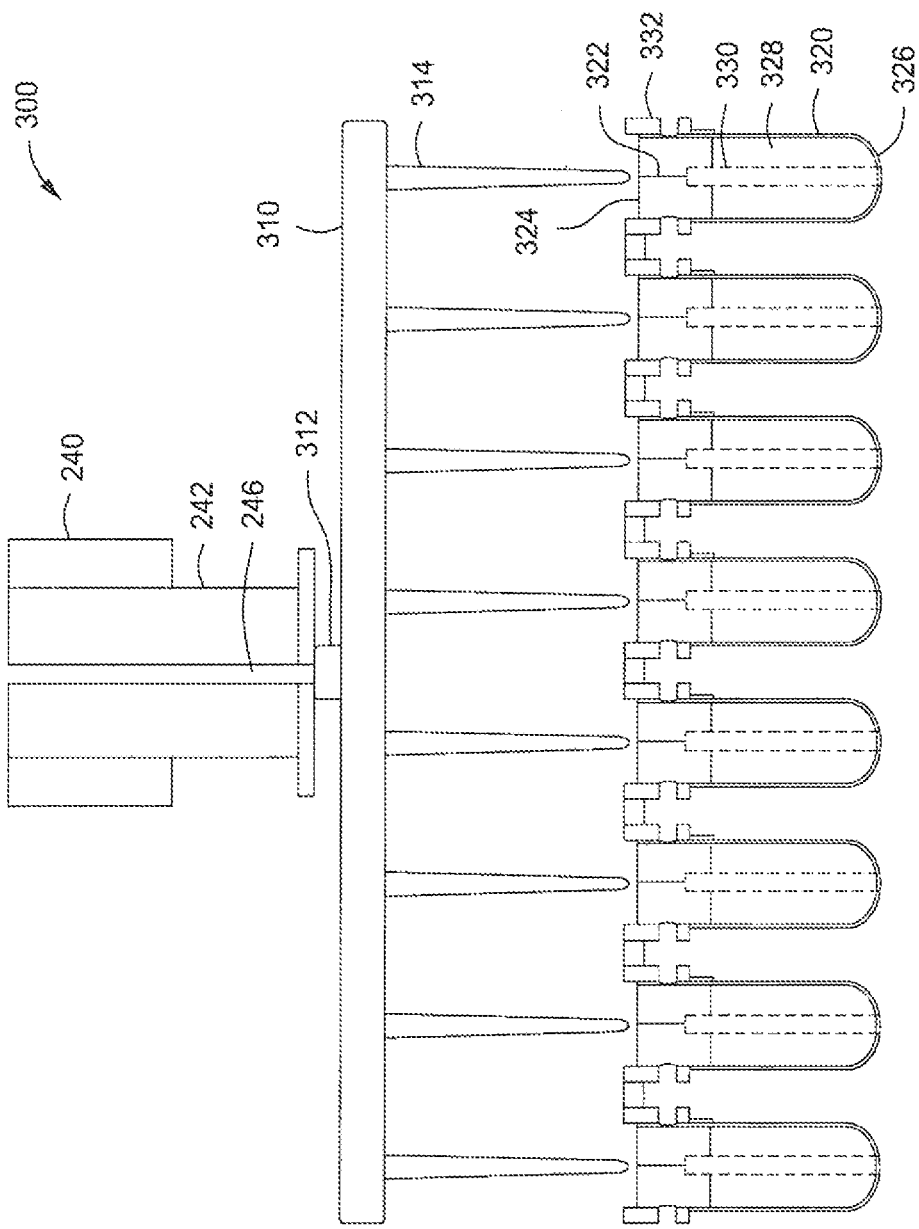
FIG. 3 depicts a cross-sectional view of the fourth injector of the preparation assembly in fluid communication with a distributor, according to one or more embodiments described.
Figure 4:
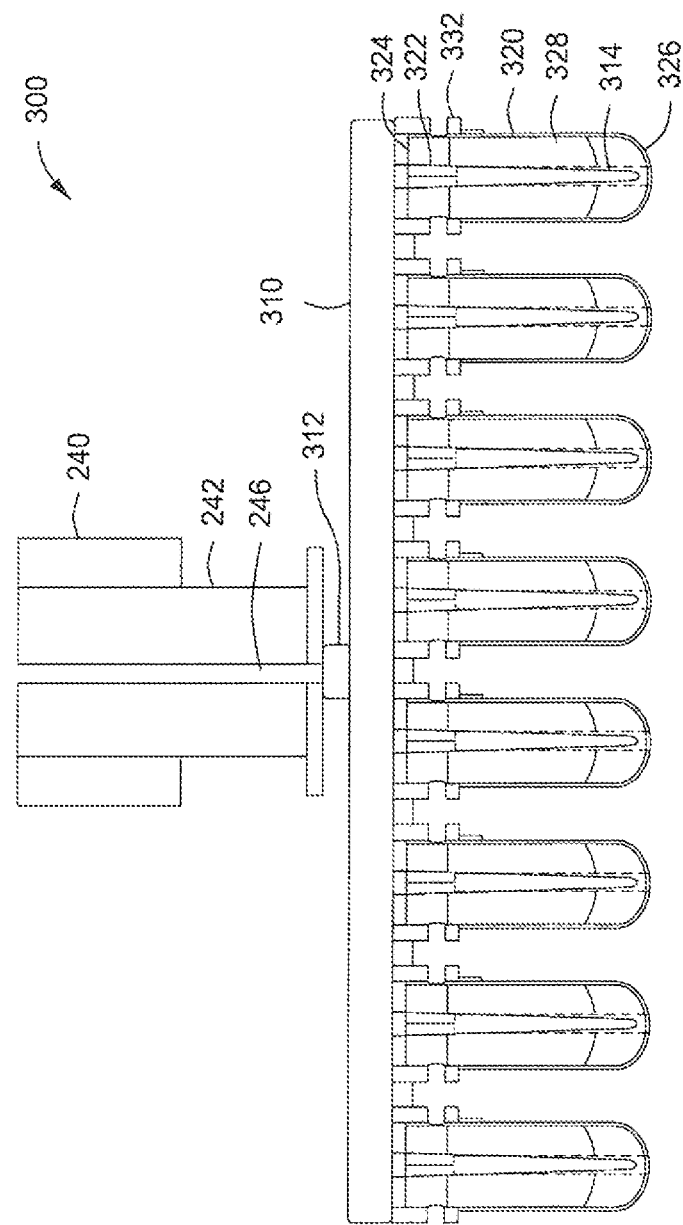
FIG. 4 depicts a cross-sectional view of the distributor in fluid communication with one or more containers, according to one or more embodiments described.

FIG. 3 depicts a cross-sectional view of the fourth injector 240 of the preparation assembly 200 in fluid communication with a distributor or manifold 310 of distribution assembly 300, and FIG. 4 depicts a cross-sectional view of the distributor 310 in fluid communication with one or more containers or tubes 320, according to one or more embodiments. The distribution assembly 300 can include the distributor 310 and one or more tubes or containers (eight are shown 320). The distributor 310 can include an inlet 312 in fluid communication with one or more outlets 314. The outlets 314 can be made of any material (plastic, metal, etc.) and sized to fit within the containers 320. In at least one embodiment, the inlet 312 can be coupled to the fourth injector 240 directly, or through a flexible conduit or tube to allow more adaptability in configuration and to allow multi-sample preparation. Further, the inlet 312 may be configured to be in fluid communication with the fourth reservoir 244 through the bore 246 in the piston 242. Each outlet 314 can be adapted to be inserted into a container 320, as shown in FIG. 4. The number of outlets 314 and/or containers 320 can range from a low of 1, 2, 4, 6, 8, or 10 to a high of about 15, 20, 25, 30, 35, 40, or more. The distributor 310 can be designed with additional inlets to communicate with the exterior to allow washing and creation of a vacuum within each container 320.

The containers 320 can be made of glass or plastic and define an internal volume. The internal volume can range from a low of about 0.25 mL, about 0.5 mL, about 1 mL, about 2 mL, about 3 mL, about 4 mL, or about 5 mL to a high of about 6 mL, about 8 mL, about 10 mL, about 15 mL, about 20 mL, or more. Each container 320 can include a seal 322 (e.g., a rubber seal) proximate a first end 324 thereof. The seal 322 can be adapted to prevent fluid from leaking into or out of the container 320. Each container 320 can also have a piston or plug 328 disposed therein and coupled to the seal 322. The plug 328 can be adapted to sealingly engage the inner walls of the container 320 and slide axially therein. The plug 328 can have a bore formed axially therethrough, and a tube 330 can be disposed within the bore. The tube 330 can have a diameter ranging from a low of about zero (0) (e.g., when the outlet 314 is not inserted), about 0.5 mm, about 1 mm, or about 2 mm to a high of about 4 mm, about 6 mm, about 8 mm, or more. Each tube 330 can be adapted to have one of the outlets 314 of the distributor 310 inserted into it.

Accordingly, each outlet 314 can extend through the seal 322, the plug 328, and/or the tube 330 to introduce fluids into the corresponding container 320. Once the outlet 314 is inserted into and in fluid communication with the container 320, the plug 328 can be moved toward the first end 324 of the container 320 generating a vacuumed space between the plug 328 and a second end 326 of the container 320. At the same time, the piston 242 (in this example the representative injector connected is injector 240) will move up to release the mixture from the fourth reservoir 244. For example, an actuator 332 can be coupled to the container 320 and adapted to move or pull the corresponding plug 328 toward the first end 324 of the container 320 to create the vacuumed space. In at least one embodiment, each container 320 can include its own actuator 332, and the actuators 332 can be coupled together to move a plurality of plugs 328 simultaneously. In another embodiment, a single actuator 332 can be adapted to move the plurality of plugs 328 in a plurality of containers 320 simultaneously. The vacuumed space can induce the fluid from the fourth reservoir 244 to flow through the bore 246 in the piston 242 and the distributor 310 and into one or more of the containers 320, as described in more detail below. Once the fluid is introduced, the seal 322 can prevent the fluids from leaking into or out of the container 320.

Now referring to FIGS. 1-4, in operation, the membrane 260 having the sample of interest, such as nucleic acids, bound thereto can be disposed within the membrane support assembly 262, and the membrane support assembly 262 can be operatively positioned within the preparation assembly 200. For example, the membrane support assembly 262 can be threadably engaged with the first injector 210 and the valve 250.

The valve 250 can be rotated to provide a first flow path 280 between the first and second reservoirs 214, 224 (see FIG. 2A). The first flow path 280 can extend through the valve 250 and the membrane 260. The second reservoir 224 can include a first reagent. The volume of the first reagent in the second reservoir 224 can range from a low of about 0.1 mL, about 0.2 mL, about 0.4 mL, about 0.6 mL, about 0.8 mL, or about 1.0 mL to a high of about 2.0 mL, about 3.0 mL, about 4.0 mL, about 5.0 mL, or more. In at least one embodiment, the first reagent can include water. In another embodiment, the first reagent can be a TE buffer (such as 10 mM Tris-Cl/1 mM EDTA, having a pH of about 7.5), an EB buffer (such as 10 mM Tris-Cl, having a pH of about 8.5), or the like. The second piston 222 can be pressed, thereby forcing the first reagent through the first flow path 280 and into the first reservoir 214. As the first reagent contacts the first membrane 260, the first reagent can cause the sample of interest, such as nucleic acids (e.g., DNA and/or RNA), bound to the first membrane 260 to release therefrom and become disposed or suspended in the first reagent, forming a first mixture in the first reservoir 214.

The first piston 212 can then be pressed, thereby forcing the first mixture back through the first flow path 280 and into the second reservoir 224. The concentration of the samples, such as the nucleic acids, within the first mixture can be measured. For example, the control system 270, operatively connected and using the light source 228, can measure the concentration of the samples of interest, such as nucleic acids, within the first mixture.

Referring now to FIG. 2B, the valve 250 can then be rotated to provide a second flow path 282 between the second and third reservoirs 224, 234. The third reservoir 234 can include a second reagent. The volume of the second reagent in the third reservoir 234 can range from a low of about 0.1 mL, about 0.2 mL, about 0.4 mL, about 0.6 mL, about 0.8 mL, or about 1.0 mL to a high of about 2.0 mL, about 3.0 mL, about 4.0 mL, about 5.0 mL, or more. In at least one embodiment, the second reagent can include water or any other suitable dilution buffer. The second piston 222 can be pressed, thereby forcing at least a portion the first mixture through the second flow path 282 and into the third reservoir 234, forming a second mixture including the first mixture and the second reagent in the third reservoir 234.

The amount of the first mixture introduced to the third reservoir 234 can depend, at least in part, on the concentration of the samples of interest, such as the concentration of nucleic acids disposed within the first mixture. For example, as the amount of the first mixture introduced to the third reservoir 234 increases, the concentration of the second mixture increases; however, as the amount of the first mixture introduced to the third reservoir 234 decreases, the second mixture becomes more diluted. In at least one embodiment, a ratio of DNA to the total volume of the first and/or second mixture can range from a low of about 0.4 ng/µL, about 0.8 ng/µL, about 1.2 ng/µL, about 1.6 ng/µL, or about 2.0 ng/µL to a high of about 3.0 ng/µL, about 4.0 ng/µL, or about 5.0 ng/µL. In another embodiment, a ratio of RNA to the total volume of the first and/or second mixture can range from a low of about 0.05 ng/µL, about 0.10 ng/µL, about 0.20 ng/µL, about 0.30 ng/µL, or about 0.40 ng/µL to a high of about 1.0 ng/µL, 1.2 ng/µL, about 1.4 ng/µL, about 1.6 ng/µL, about 1.8 ng/µL, or about 2.0 ng/µL.

The valve 250 can then be rotated to provide a third flow path 284 between the third and fourth reservoirs 234, 244 (see FIG. 2C). The fourth reservoir 244 can include a third reagent. The volume of the third reagent in the fourth reservoir 244 can range from a low of about 0.1 mL, about 0.2 mL, about 0.4 mL, about 0.6 mL, about 0.8 mL, or about 1.0 mL to a high of about 2.0 mL, about 3.0 mL, about 4.0 mL, about 5.0 mL, or more. In at least one embodiment, the third reagent can include a Polymerase Chain Reaction (PCR) master mix. The PCR master mix can include DNA polymerase, a buffer, and deoxynucleoside triphosphates (dNTPs). Suitable PCR master mixes can include the Taq PCR Master Mix commercially available from Qiagen, Inc. in Valencia, Calif. In at least one embodiment, when the second mixture includes RNA as the sample of interest, the second mixture can be mixed with reverse transcriptase prior to being combined with the PCR master mix in the fourth reservoir 244. In another embodiment, the reverse transcription polymerase chain reaction can be completed in a single step. When the preparation assembly 200 is coupled with another assembly (not shown), such as the isolation assembly shown and described in U.S. patent application Ser. No. 13/461,487 entitled "System and Method for Isolation of Samples," the entire content of which is hereby incorporated herein by reference, the RNA and reverse transcriptase can be injected first to complete reverse transcription, and then PCR mix can be injected from another reservoir to complete PCR.

Following the rotation of valve 250 to provide third flow path 284, the third piston 232 can be pressed, thereby forcing at least a portion of the second mixture through the third flow path 284 and into the fourth reservoir 244, forming a third mixture including the second mixture and the third reagent. In at least one embodiment, the valve 250 can then be rotated to form the flow path 280 (as shown in FIG. 2A) or the flow path 282 (as shown in FIG. 2B), particularly when only one bore is present within valve 250, such that the valve 250 is "closed" to the fourth reservoir 244. In another embodiment, a second bore may be present within valve 250 that is constructed with a check valve to permit flow of fluid in only one direction, such as in this embodiment from the third reservoir 234 to the fourth reservoir 244, thereby preventing back flow of the third mixture and effectively "closing" the fourth reservoir 244 in an alternate manner. In at least one embodiment, the actuators 332 can then move the plugs 328 toward the first end 324 of the containers 320 inducing the vacuumed space between the plugs 328 and the second end 326 of the containers 320 (see FIGS. 3 and 4). The vacuumed space can induce the third mixture to flow from the fourth reservoir 244 through the bore 246 in the piston 242 and toward the distributor 310. In another embodiment, the piston 242 of the fourth injector 240 can be pressed forcing the third mixture through the bore 246 in the piston 242 and toward the distributor 310.

The third mixture can flow into the distributor 310 via the inlet 312 and split or be divided among one or more outlets 314. The third mixture can then flow out the distributor 310 via the outlets 314 and into the containers 320, as shown in FIG. 4. The third mixture can be introduced to the vacuumed space in the containers 320 between the second end 326 and the plug 328. In at least one embodiment, the containers 320 can include a fourth reagent (which may be dried or liquid) disposed therein. Thus, the third mixture can be combined with the fourth reagent in the containers 320 to form a fourth mixture therein. The volume of the fourth reagent in each container 320 can range from a low of about zero (0, i.e., dried form), 0.01 mL, about 0.02 mL, about 0.05 mL, about 0.10, about 0.2 mL, about 0.5 mL, or about 1.0 mL to a high of about 2.0 mL, about 3.0 mL, about 4.0 mL, about 5.0 mL, or more. In at least one embodiment, the fourth reagent can be suspended, or bind to the bottom of the container, including oligonucleotide primers, probes, enzymes, buffers, inhibitors, activators in either dried form or liquid form, fluorophore labeled or colorimetric analysis, or the like.

Once the third mixture has been introduced to the containers 320, the outlets 314 of the distributor 310 can then be withdrawn from the containers 320. The seals 322 and the plugs 328 can secure the fourth mixture within the containers 320. A cap (not shown) can also be placed on the first end 322 of the container 320 to add an additional sealing element. For example, the cap can be threaded onto the first end 322 of the container 320. The container 320 can then be used for polymerase chain reactions or other processes.

Figure 5A:
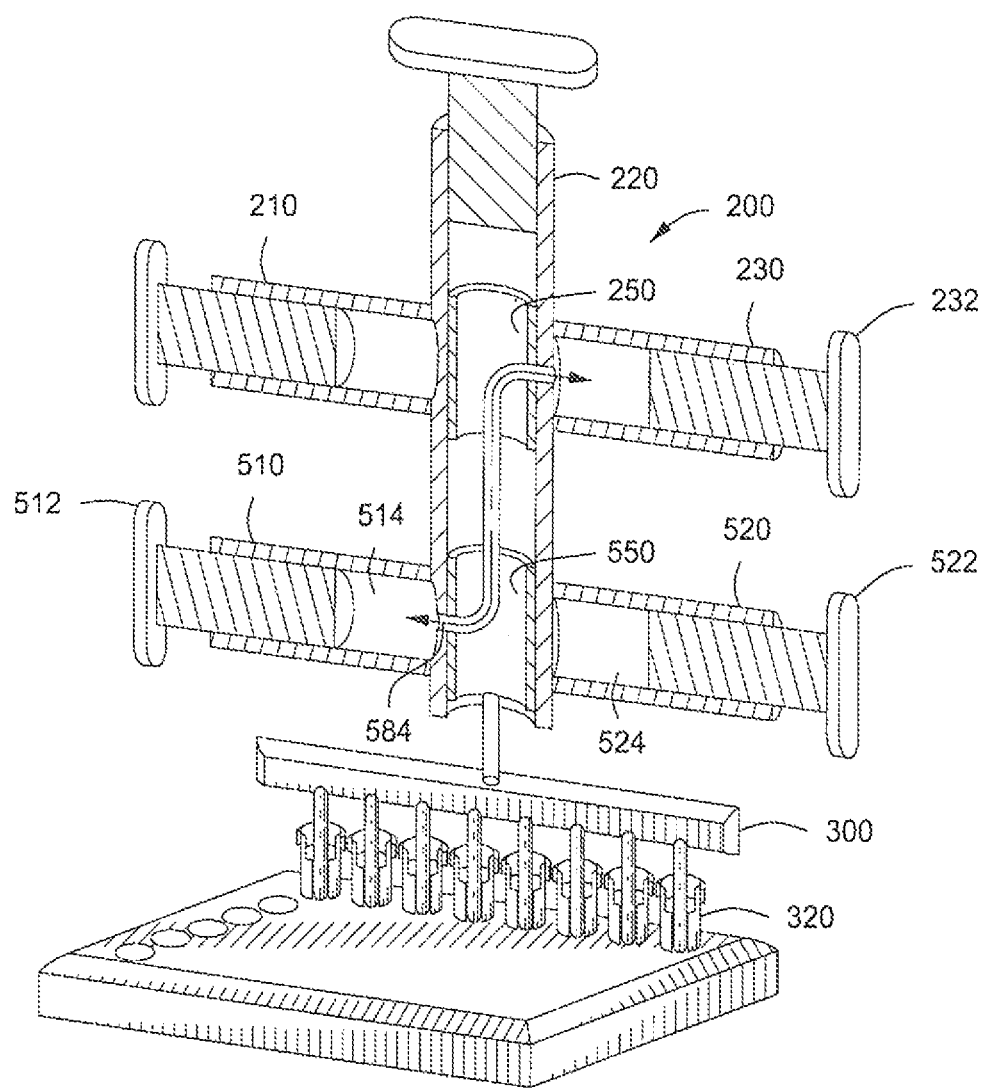
FIGS. 5A-5C depict partial cross-sectional perspective views of another illustrative embodiment of a sample preparation assembly having a second valve in fluid communication with the containers via the distributor, according to one or more embodiments described.
Figure 5B:
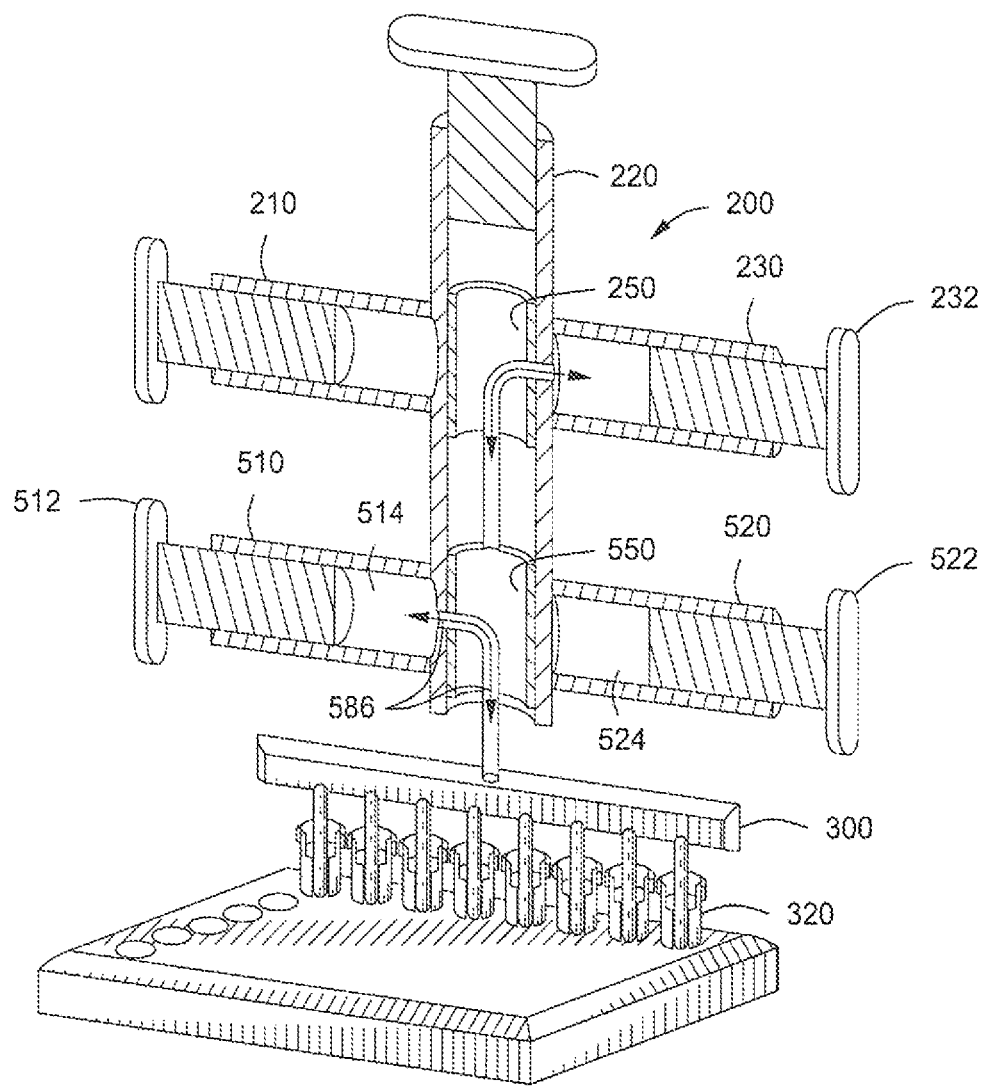
Figure 5C:
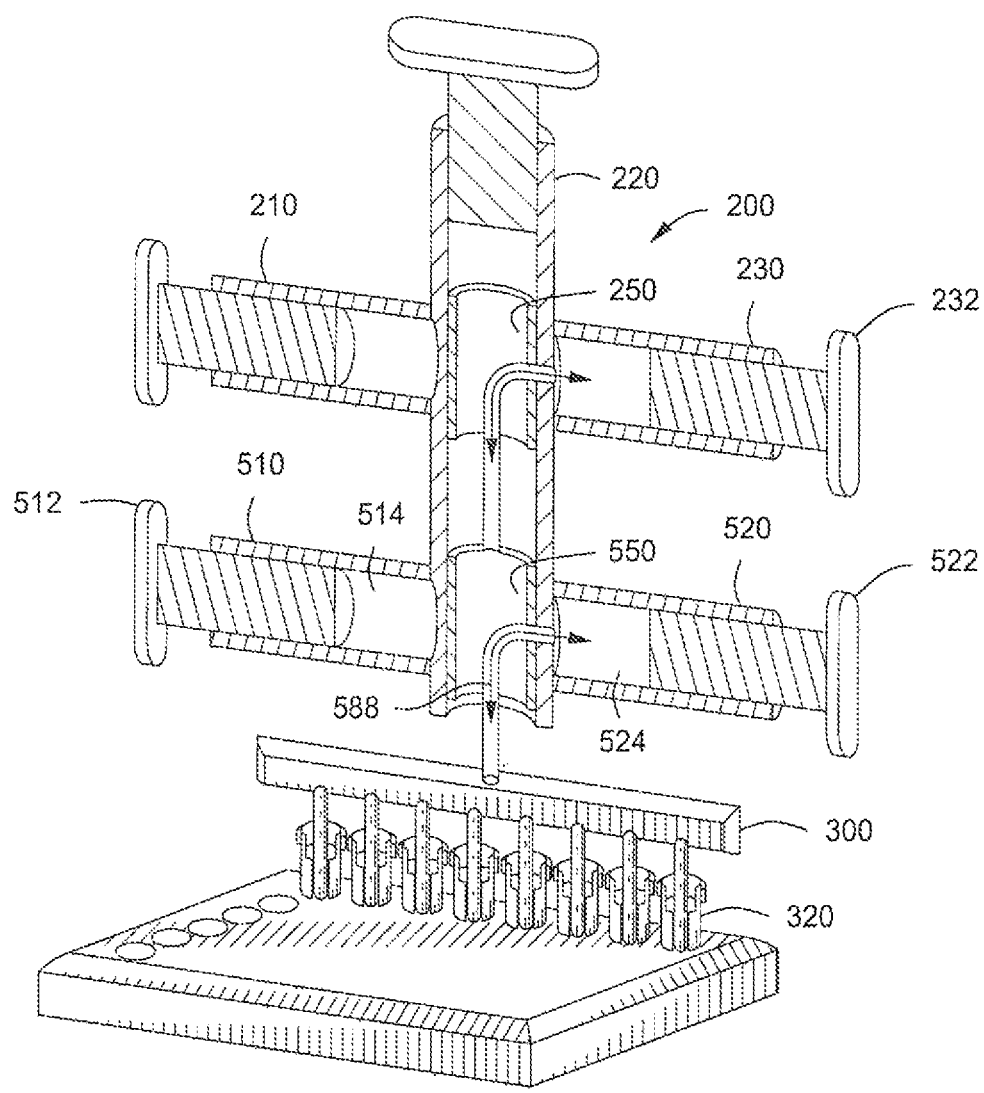

FIGS. 5A-5C depict perspective cross-sectional views of another illustrative embodiment of the preparation assembly 200 in fluid communication with the containers 320 via the distributor assembly 300, according to one or more embodiments. As shown, the preparation assembly 200 can include a second valve 550 in fluid communication with the first valve 250. In another embodiment, the preparation assembly 200 can include a second valve 550 in fluid communication with the fourth injector 240 (not shown). One or more injectors (two are shown 510, 520) can be coupled to the second valve 550.

In at least one embodiment, the first and second valves 250, 550 can be rotated to form a flow path into a fifth reservoir 514 in the fifth injector 510. Referring to FIG. 5A, the third piston 232 can be pressed, thereby forcing at least a portion of the second mixture through the flow path 584 into the fifth reservoir 514, forming a third mixture including the second mixture and a fourth reagent. The fourth reagent can include any one or more of the reagents discussed above.

The second valve 550 can then be rotated to provide a flow path 586 as shown in FIG. 5B between the fifth reservoir 514 and the containers 320 (via the distributor assembly 300). The fifth piston 512 can be pressed, thereby forcing at least a portion of the third mixture through the distributor assembly 300 and into at least one of the containers 320. As shown in FIG. 5C, the second valve 550 can then be rotated to form a flow path 588 between the sixth reservoir 524 and the containers 320 via the distributor assembly 300. The sixth piston 522 can then be pressed, thereby forcing at least a portion of a fifth reagent into the containers 320 to mix with the third mixture. The fifth reagent can include any one or more of the reagents discussed above.

In at least one embodiment, prior to transferring the mixture (e.g., from the fifth reservoir 514 and/or the sixth reservoir 524, or from the fourth reservoir 244) from the preparation assembly 200 to the containers 320 via the distributor assembly 300, the distributor 310 can be soaked or rinsed in one or more buffers (such as by placement in a container of buffer solution or by introducing buffer(s) through the inlet 312). Suitable buffers can include, but are not limited to, deionized water, ribonuclease (RNase) free water, or the like. After soaking in the buffer solution, the mixture can be drawn into the distributor 310 until the mixture approaches the tip of the outlets 314. At this time, the outlets 314 can be inserted into the containers 320. By drawing the mixture into the distributor 310 and proximate the tip of the outlets 314, bubbles may be reduced or prevented in the containers 320.

Figure 6:
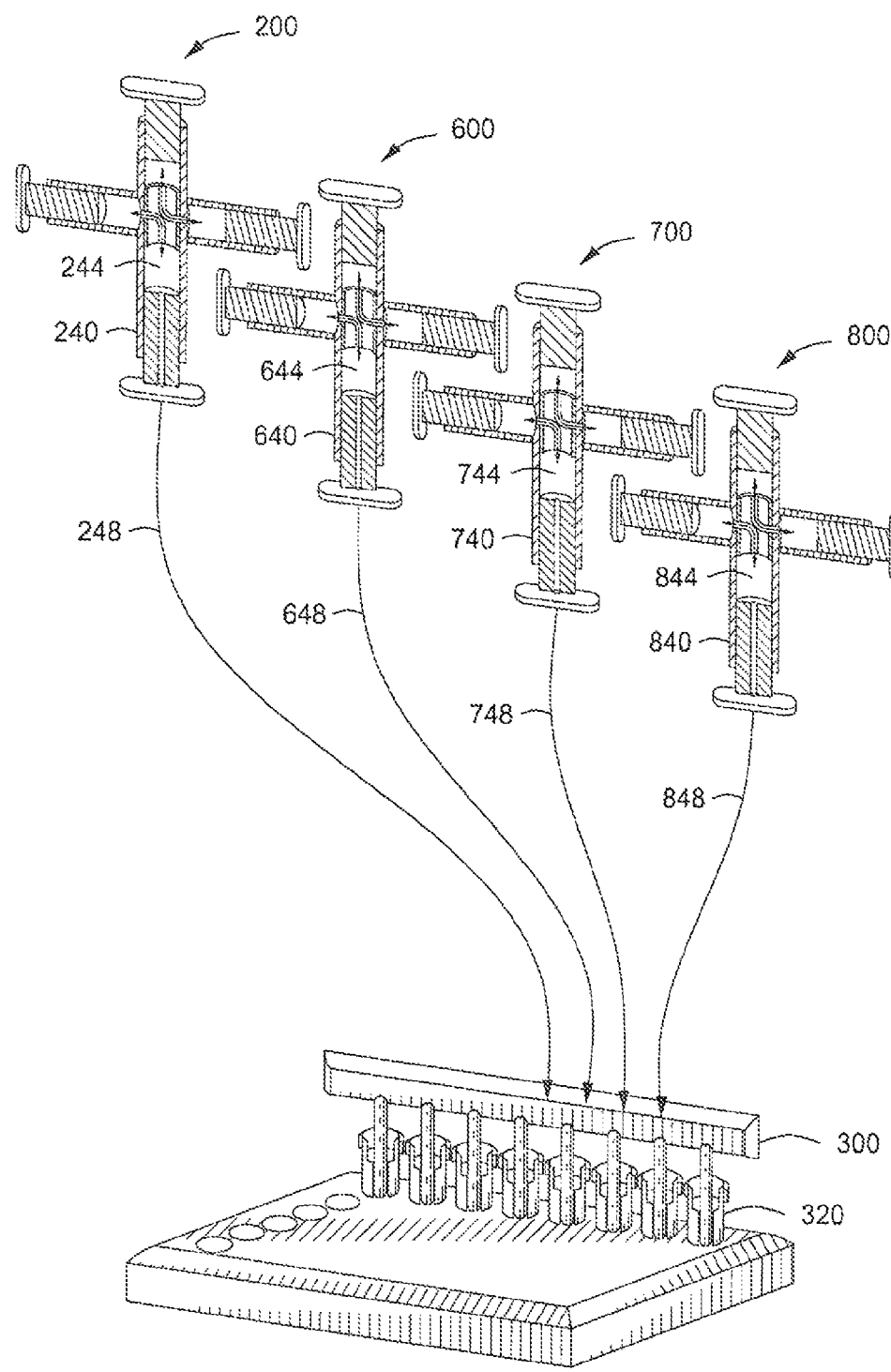
FIG. 6 depicts a perspective view of a plurality of preparation assemblies in fluid communication with the containers via the distributor, according to one or more embodiments described.

FIG. 6 depicts a perspective view of a plurality of preparation assemblies 200, 600, 700, 800 in fluid communication with the containers 320 via the distributor assembly 300, according to one or more embodiments described. A plurality of preparation assemblies (four are shown 200, 600, 700, 800) can be in fluid communication with the containers 320 via the distributor 310. As shown, tubes 248, 648, 748, 848 may be coupled respectively to the corresponding fourth injector 240, 640, 740, 840 of each preparation assembly. Tubes 248, 648, 748, 848 may provide a path of fluid communication from each respective fourth reservoir 244, 644, 744, 844 to the distributor assembly 300. Each tube 248, 648, 748, 848 can be coupled to the same distributor assembly 300, or each tube 248, 648, 748, 848 can be coupled to a different distributor assembly (not shown).

Certain embodiments and features have been described using a set of numerical upper limits and a set of numerical lower limits. It should be appreciated that ranges from any lower limit to any upper limit are contemplated unless otherwise indicated. Certain lower limits, upper limits, and ranges appear in one or more claims below. All numerical values are "about" or "approximately" the indicated value, and take into account experimental error and variations that would be expected by a person having ordinary skill in the art. The reagents listed are mainly for real-time PCR or RT-PCR. For other applications, such as enzymatic assay, luminal assay, ELISA, the reagents may vary.

Various terms have been defined above. To the extent a term used in a claim is not defined above, it should be given the broadest definition persons in the pertinent art have given that term as reflected in at least one printed publication or issued patent. Furthermore, all patents, test procedures, and other documents cited in this application are fully incorporated by reference to the extent such disclosure is not inconsistent with this application and for all jurisdictions in which such incorporation is permitted.

Although only a few exemplary embodiments have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims. In the claims, means-plus-function and step-plus-function clauses are intended to cover the structures or acts described herein as performing the recited function and not only structural equivalents, but also equivalent structures. Thus, although a nail and a screw may not be structural equivalents in that a nail employs a cylindrical surface to secure parts together, whereas a screw employs a helical surface, in the environment of fastening parts, a nail and a screw may be equivalent structures.

What is claimed is:

1. A preparation system, comprising:
    a first injector having a first reservoir disposed therein;
    a second injector having a second reservoir disposed therein;
    a valve disposed between the first and second reservoirs such that a path of fluid communication exists between the first and second reservoirs through the valve;
    a membrane disposed between the first reservoir and the valve such that the path of fluid communication extends through the membrane;
    a distributor having an inlet coupled to the second injector and in fluid communication with the second reservoir; and
    one or more containers coupled to an outlet of the distributor, wherein a reagent when disposed in the second reservoir is capable of flowing from the second reservoir, through the distributor, and into the one or more containers.

2. The preparation system of claim 1, wherein the second injector comprises a piston having a bore formed therethrough, and wherein the second reservoir is in fluid communication with the inlet of the distributor through the bore.

3. The preparation system of claim 1, wherein the membrane comprises nucleic acids bound thereto, and wherein when a reagent disposed in the second reservoir contacts the membrane, at least a portion of the nucleic acids are adapted to release from the membrane and become disposed within the reagent.

4. The preparation system of claim 1, further comprising a reagent disposed in the second reservoir.

5. The preparation system of claim 4, further comprising a third injector coupled to the valve and having a third reservoir disposed therein, wherein the third reservoir comprises a polymerase chain reaction master mix disposed therein.

6. The preparation system of claim 1, wherein each of the one or more containers comprises a plug disposed therein, wherein the plug is adapted to sealingly engage an inner wall of the container.

7. The preparation system of claim 1, wherein the one or more containers are pre-vacuumed by moving a plug disposed therein.

8. A method for preparation of a biological sample for analysis using the preparation system of claim 1, wherein the method comprises contacting the biological sample with a reagent adapted to flow from the second reservoir, through the valve and the membrane, and into the first reservoir.

9. The method of claim 5, wherein the reagent comprises between about 0.1 mL and about 3.0 mL of water.

10. The method of claim 8, wherein the reagent comprises between about 0.1 mL and about 3.0 mL of a polymerase chain reaction master mix.

11. The preparation system of claim 1, wherein the second injector comprises a piston disposed at least partially therein, and wherein a bore extends through the piston such that the bore is in fluid communication with the second reservoir.

12. The preparation system of claim 1, further comprising a spectrophotometer in communication with an interface on the first injector, the second injector, or both.

13. The preparation system of claim 1, wherein at least one of the first and second injectors is threadably engaged with the valve.

14. A method of releasing nucleic acids from a membrane, comprising:
    providing a self-contained preparation system comprising a first reservoir, a second reservoir, a membrane for collecting nucleic acids disposed between the first reservoir and the second reservoir, and a valve disposed between the first reservoir and the second reservoir and the membrane such that a path of fluid communication exists between the first and second reservoirs through the valve;
    flowing a first reagent through a first flow path between the first reservoir and the second reservoir, wherein the first flow path extends through the valve and the membrane, and wherein nucleic acids are released from the membrane when contacted with a first reagent to form a first mixture comprising the first reagent and the released nucleic acids;
    positioning the valve to form a second flow path between the second reservoir and a third reservoir through the valve; and
    flowing at least a portion of the first mixture through the second flow path and into the third reservoir containing a second reagent to form a second mixture.

15. The method of claim 14, wherein at least one of the first and second reagents comprises water.

16. The method of claim 14, further comprising measuring a concentration of the nucleic acids disposed within the first mixture.

17. The method of claim 14, further comprising flowing the second mixture through a distributor and into one or more containers for further analysis.

* * * * *